United States Patent [19]

Li

[11] Patent Number: 5,206,028
[45] Date of Patent: Apr. 27, 1993

[54] DENSE COLLAGEN MEMBRANE MATRICES FOR MEDICAL USES

[76] Inventor: Shu-Tung Li, 1 Kiowa Ter., Oakland, N.J. 07436

[21] Appl. No.: 653,178

[22] Filed: Feb. 11, 1991

[51] Int. Cl.$^5$ ................................................ A61K 9/14
[52] U.S. Cl. .................................... 424/484; 424/443; 424/445; 424/447; 424/491
[58] Field of Search ............... 424/484, 443, 445, 447, 424/491, 423; 530/356; 514/801

[56] References Cited

U.S. PATENT DOCUMENTS

| | | | |
|---|---|---|---|
| 4,703,108 | 10/1987 | Silver et al. | 514/801 |
| 4,795,467 | 1/1989 | Piez et al. | 514/801 |
| 4,863,856 | 9/1989 | Dean, Jr. et al. | 530/356 |
| 5,024,841 | 6/1991 | Chu et al. | 530/356 |

*Primary Examiner*—Thurman K. Page
*Assistant Examiner*—D. Colucci
*Attorney, Agent, or Firm*—Caesar, Rivise, Bernstein, Cohen & Pokotilow, Ltd.

[57] ABSTRACT

The present invention is directed to collagen membranes having physical and biological properties which make them extremely suitable and desirable for all types of medical uses, particularly as a periodontal barrier. The membranes are characterized by having a surface roughness morphology similar to leather and are translucent. Moreover, these membranes do not swell appreciably upon being wetted so as to maintain their overall bulk density. Methods for preparing these membranes and applications for their use are also disclosed.

28 Claims, No Drawings

DENSE COLLAGEN MEMBRANE MATRICES FOR MEDICAL USES

BACKGROUND OF THE INVENTION

1. Field of the Invention

This invention pertains to the field of collagen membrane matrices. More specifically, the present invention relates to collagen membranes having physical and biological properties which make them extremely suitable and desirable for all types of medical uses, particularly as a periodontal barrier. Methods for preparing these membranes and applications for their use are also disclosed.

2. Discussion of Related Art

Collagen has been used extensively in medicine and in surgery. Collagen is a fibrous protein and constitutes the major protein component of skin, bone, tendon, ligament, cartilage, basement membrane and other forms of connective tissue. It is the most abundant protein in the animal kingdom. In bone, for example, collagen fibers reinforce the calcium phosphate mineral base. Despite its great strength, bone retains flexibility because of its collagen content.

Collagen based devices have been used as nerve regeneration tubes, as sutures, hemostatic fiber and sponges, wound dressings, neurosurgical sponges, injectable implants for soft tissue augmentation, pharmaceutical carriers, opthalmic aqueous-venous shunts, contact lenses and the like.

The properties of collagen which favor its use as a biomaterial are many. It has a high order of tensile strength and low extensibility. Collagen is biodegradable, and when implanted in the body, is absorbed at a rate that can be controlled by the degree of intra or intermolecular cross-linking imparted to the collagen molecule by chemical or physical treatment. Collagen products can thus be designed such that, on implantation, they will completely be absorbed in a few days or in months. The collagen can also be chemically treated so that it becomes non-absorbable while still retaining its hydrophilic character and its good tissue response. Although native collagen is a very weak antigen, it can be made, for all practical purposes, immunologically inert by means well known to those skilled in the art.

The collagen molecule is a triple helix and has a unique protein configuration that is a coiled coil of three polypeptide subunits or alpha chains. Each alpha chain twists in a left-handed helix with three residues per turn, and three chains are wound together in a right-handed superhelix to form a rod-like molecule about 1.4 nanometers in diameter and 300 nanometers long. The alpha chains each contain about 1,050 amino acid residues and the molecular weight of the collagen molecule is about 300,000. In each alpha chain within the triple helix every third amino acid residue is glycine. Collagen is characterized by a high content of proline and hydroxyproline amino acids, the absence of tryptophane, a minor amount of aromatic amino acids, and a significant amount of dicarboxylic and dibasic amino acids. At both ends of the collagen molecule there are terminal peptide sequences known as telopeptides which are globular and not triple helical in structure and which lack glycine at every third residue. These telopeptides are the primary sites of inter-molecular cross-linking in the molecule and are the most antigenic portions of the collagen molecule.

The collagen molecule which is elaborated by fibrogenic cells aggregate in the extracellular matrix of connective tissue to form fibrils which range from 10 to 200 nanometers in diameter. The collagen fibrils aggregate into collagen fibers.

The main sources of collagen for commercial applications are bovine tendons, calf, steer or pig hide. All are readily available at relatively low cost. Generally, reconstituted collagen products are prepared by purification of native collagen by enzyme treatment and chemical extraction. The purified collagen is then dispersed or dissolved in solution, filtered and retained as such, or is reconstituted into fiber, film or sponge by extrusion or casting techniques which are well known to those skilled in the art.

Although the collagen of skin, tendons, bone, cartilage, blood vessels and basement membrane are similar in structure and composition, they do differ slightly in relative amino acid content, amino acid sequence and in architecture. They are products of different genetic loci. The different genetic collagens are known as Type I, II, III, IV, V, etc. The collagen of native skin, tendons, ligaments and bone are primarily Type I collagen with which the present invention is directed.

Generally, regardless of the particular genetic collagen that is utilized, when in the form of a dry film, it will typically be transparent and have a morphology which has a feel not unlike that of a thin sheet of plastic. When wetted, the collagen film material, in addition to being transparent, now becomes slippery and slimy as well. While such a transformation may have little, if any, effect upon the performance of the collagen film material when it has already been affixed in position for its intended use prior to such transformation, it may create numerous problems and disadvantages if such transformation takes place prior to such utilization, which is generally the case. Thus, in many instances, it is necessary for the physician or dentist to work with the collagen film material in a manner such that it will readily contour itself to the surface upon which it is being applied. For example, when utilizing a collagen film as a wound covering, the dry and relatively rigid membrane will not easily conform to the wound and its shape without first being wetted. Once wetted, the collagen film will easily conform to the shape of the wound being treated. However, the transparency and slipperiness of the collagen film makes it extremely difficult for the doctor to properly handle and see, particularly when a relatively small wound area is being treated. This is even further made difficult when, as is conventionally done, the collagen film is to be sutured.

Such a disadvantage is particularly noticeable when a collagen film is utilized as a periodontal barrier. More specifically, with advanced periodontal disease, after the root surface has been surgically exposed and debrided, it is desirable to place a membrane over these areas and then have the mucoperiosteal flaps adapted over such membrane and sutured. The membrane helps prevent epithelim and gingival connective tissue from contacting the root of the tooth during healing, thereby allowing the area to be repopulated with cells originating from the periodontal ligament. This is the basis for what is known in the art today as "guided tissue regeneration." However, in order to be so utilized, if the membrane is made of collagen in the form of a rigid film, it must first be wetted causing it to be not only transparent but also slippery and slimy as well. In view of the small area that needs to be covered with this film as a periodontal barrier, the transparency, sliminess and slipperiness of this material makes it extremely difficult, if not practically impossible, for the user to handle. Still further, the transparency and morphology of the wetted collagen film material makes it extremely difficult to ascertain that the film is properly positioned in the surgical site making it a less than an ideal material for periodontal surgery.

Moreover, the rate of resorption of a collagen film material in the body may not always be easily controllable to the extent desired such that resorption occurs when most advantageous, particularly in periodontal surgery. In such applications, it is desirable to have an intact collagen film for a predetermined period of time after implantation, to be subsequently resorbed at a faster rate. However, the resorption of conventional collagen films generally starts and remains at the surface which is in contact with the body inasmuch, as we have found, the pore size of such collagen films does not readily permit enzymes to penetrate into the inner layers of the film to allow for uniform, controlled resorption.

The use of a collagen membrane as a periodontal barrier is described in, for example, "The Use of Collagen Membranes to Guide Regeneration of New Connective Tissue Attachment in Dogs" by Neil M. Blumenthal, *Journal of Periodontology*, Volume 59, No. 12, pgs. 830-836 (1988). While other membrane materials have been utilized as periodontal barriers, such as Teflon membranes, as discussed in, for example, "New Attachment Formation in the Human Periodontium by Guided Tissue Regeneration" by Jan Gottlow, et al., *Journal of Clinical Periodontology*, 13:604-616 (1986) and "New Attachment Achieved by Guided Tissue Regeneration in Beagle Dogs" by R. G. Caffesse, et al., *Journal of Periodontology*, Volume 59, No. 9, pgs. 589-594, such other materials suffer from the major disadvantage of not being resorbable by the body. Instead, these alternative materials must be removed by yet a second surgical procedure.

A need accordingly exists for a collagen material, particularly a collagen membrane, which does not become slippery, slimy and transparent when wetted. A need also exists for such a collagen material to have a relatively constant, predetermined controlled density which facilitates in vivo resorption. Still further, it would also be desirable to have a collagen membrane with a predetermined, relatively constant permeability, i.e., a pore size, which will be particularly amenable to allowing specific constituents through the membrane, such as nutrients, enzymes and macromolecules, while effectively preventing the diffusion of undesirable constituents, such as fibrogenic cells. In conjunction with these needs, the collagen material still needs to have excellent mechanical strength and controlled high resorptivity. Such needs are particularly desirable in the field of periodontology.

SUMMARY OF THE INVENTION

By means of the present invention, a new method for making a collagen membrane matrix material has been discovered which collagen membrane essentially eliminates all of the above-noted disadvantages and problems associated with the prior art collagen films, particularly for use in medical applications such as in periodontology.

More particularly, by means of the present invention, a collagen membrane matrix material has been discovered which has excellent structural integrity, both when wet and dry; has a surface roughness morphology which makes it very easy to handle, even while wet; when dry, it is white, opaque and has a morphology and feel which is similar to bond paper; when wetted, it becomes translucent and has a leather-like rough texture making it easy to work with; and has a high, controllable rate of resorption in the body. In contrast to conventional collagen films, the collagen membrane matrix material of the present invention is characterized by not being transparent, either when wet or dry and by having a rough texture which is not slimy or slippery as in conventional collagen films thereby making it is easy to handle and work with, particularly when wetted with water.

Preferably, the collagen membrane material has a pore size in the range of from about 0.003 $\mu$m to about 0.10 $\mu$m, and preferably is in the range of from about 0.005 $\mu$m to about 0.01 $\mu$m. This pore size is optimal for effectively controlling the permeability of the membrane so as to allow selective diffusivity wherein desirable nutrients and macromolecules are able to diffuse through the membrane and enter the site of the wound so as to facilitate healing while at the same time prevent the introduction of undesirable elements such as epithelium and gingival connective tissue in the case of periodontal therapy. Moreover, this pore size also allows for enzymes to penetrate the inner structure of the membrane thereby facilitating resorption of the membrane matrix. This is in contrast to conventional collagen films which are generally less permeable.

The bulk density of the collagen membrane matrix of the present invention can be controlled and is desirably in between that of a collagen sponge, at its minimum, and a collagen film, at its maximum. Typically, its density will be in the range of from about 0.5 to about 1.5 g/cc, and preferably about 0.8 to about 1.2 g/cc.

Moreover, the membrane matrix of the present invention is characterized by a solution uptake of from about 1.2 to about 3.2 g/g and a suture pull-out strength of from about 30 to about 150 grams. Generally, a suture strength of from about 20 to 30 grams is typically considered in the art as being sufficient to provide enough strength to provide adequate suturing ability.

Still further, the membrane matrix of the present invention is also characterized by a 45 degree bending strength of from about 5 to about 30 grams, a measure of its excellent handleability. Its shrinkage temperature, which is indicative of its resorption capability, is in the range of from about 55° to about 75° C. It also is characterized by a light transmittance of from about 0% to about 10% and a rolling resistance of from about 0.15 to about 0.5 mm, characteristics which provide for its excellent handleability and its non-slimy, non-slippery and translucent appearance when wet.

Generally, the dense collagen membrane matrix materials of the present invention are prepared by forming a collagen sponge, comprising insoluble collagen, most preferably Type I collagen, which is then compressed and treated so as to obtain a predetermined, desired bulk density. This density will not vary substantially once the membrane is prepared in accordance with the present invention. Thus, even after the membrane is wetted, either before application onto a surgical site or wound or, alternatively, while it is in place in the body, it will not appreciably swell or expand thereby desirably retaining its dimensions and resorptivity, as well as its bulk density. Typically, the amount of swelling that does occur when wetted is in the range of from about 50 to about 70% based on the original thickness dimensions of the unwetted membrane.

More particularly, the method for making the dense collagen matrix material of the present invention, which material is translucent and non-slippery comprises the steps of:

a) forming an aqueous dispersion containing Type I collagen:

b) freezing the aqueous dispersion:

c) subjecting the frozen dispersion to freeze-drying conditions to remove frozen water and form a collagen sponge matrix;

d) subjecting the collagen sponge matrix to humidification conditions;

e) compressing the humidified collagen sponge matrix;

f) cross-linking the compressed collagen matrix by treatment with a cross-linking agent;

g) refreezing the cross-linked collagen matrix;

h) resubjecting the frozen collagen matrix to freeze-drying conditions to remove frozen water;

i) resubjecting the dried cross-linked collagen matrix to humidification conditions; and then j) further compressing the humidified, collagen matrix to form the dense collagen membraneous matrix material.

The collagen membranes of the present invention are applicable for essentially any medical use that is conventionally used with collagenous materials and offers the additional advantages of improved structural integrity, high controllable rate of resorption, translucency, non-slipperiness, and relatively constant density with no substantial swelling upon being wetted. Such medical uses include, but are not limited to, hemostatic applications, nerve regeneration conduits, blood vessel repair, uterus repair, reconstruction of lumen surfaces, tendon replacements, artificial skin, wound dressings, neurosurgical sponges, injectable implants for soft tissue augmentation, pharmaceutical carriers, opthalmic aqueous-venous shunts, contact lenses, and the like. Most preferably, the collagen membranes of the present invention are applicable as a barrier in periodontology and implantology of oral surgery.

Specifically, the collagen membranes of the present invention may be used in a method of treating a patient having periodontitis by surgically exposing the root surface of a tooth, debriding the exposed area and placing a membrane over the debrided root surface so as to prevent epithelium and gingival connective tissue from contacting the root surfaces during healing, the improvement which comprises using a collagen membrane matrix having a density of from about 0.5 to about 1.5 g/cc, which when wetted with water is translucent, non-slimy and non-slippery.

DETAILED DESCRIPTION OF THE INVENTION

The primary constituent of the collagen membrane matrix materials of the present invention is Type I collagen in its insoluble form. The collagen of native skin, tendons, ligaments and bone are primarily Type I collagen with which the present invention is directed.

The Type I collagen is retained in its natural insoluble form by keeping its natural cross-links intact by not subjecting it, as is typical in the prior art, to an enzyme treatment which would cleave its peptide linkages and form the monomeric form of the collagen. The monomeric form of the collagen is a soluble collagen and is typically referred to as atelocollagen. Instead, the collagen utilized in the present invention is in its insoluble form, i.e., it remains polymeric.

In preparing the membranes of the present invention, a collagen dispersion is first prepared in a manner well known in the art. One such preparation is taught in U.S. Pat. No. 3,157,524, which is incorporated herein by reference as if set out in full. Another preparation of collagen is also taught in U.S. Pat. No. 3,520,402 which is also incorporated herein as if set out in full.

In particular, the collagen dispersions of the present invention may be prepared by the following methods. Firstly, a native source of Type I collagen, such as, skin, tendons, ligaments or bone is first mechanically or hand cleaned of fat, fascia and other extraneous matter and washed. The cleaned and washed collagen containing material is then comminuted, generally by slicing or grinding.

The material is then subjected to an enzyme treatment while under intermittent stirring with a proteolytic enzyme such as ficin, pepsin, and the like, so as to remove non-collagenous impurities which may cause antigenic activity and to swell the collagen by removing elastin. The amount of enzyme added to the collagen material and the conditions under which enzyme digestion takes place is dependent upon the particular enzyme being used. Generally, when using ficin, which is commonly used, the pH is adjusted to about 6.0 to 6.3, and the collagen material is digested for about 1 to 2 hours at a temperature of about 36.5° C. to 37.5° C. with one part ficin for every 150 parts of collagen material. After the requisite amount of time, the enzyme is inactivated by appropriate means well known in the art such as by the addition of a solution of sodium chlorite as in the case when ficin is used.

The enzyme treated collagen containing material is then washed to remove excess enzyme and the non-collagenous protein impurities. Preferably, the washing is carried out with ultrafiltered and deionized water and optionally further washed with dilute aqueous hydrogen peroxide.

The collagen material is then further swollen with a suitable acid solution which acid does not cause any cross-linking of the collagen. Such acids are well known to those skilled in the art and include acetic acid, hydrochloric acid, lactic acid, and the like. Regardless of which acid is used, the pH of the acid collagen dispersion is in the range of from about 2 to 3.

The dispersed collagen mixture is then homogenized by any conventional means such as a blender or homogenizer so as to further dissociate the fibers and then filtered to remove unswollen, non-collagenous material by means well known in the art such as by passing the dispersion through a 100 mesh stainless steel screen. The resulting filtered collagen dispersion may then be used to prepare the collagen membrane matrix materials of the present invention.

In one embodiment of the present invention, if the collagen membrane is intended to function as a medicinal delivery vehicle, then in addition to the Type I collagen, other additives may optionally also be present in the dispersion such as medicaments, antibiotics, heparin, heparan sulfate proteoglycan, glycosaminoglycans such as hyaluronic acid, chondroitin sulfate and others, growth hormones such as epidermal growth factor (EGF), nerve growth factor, glycoproteins such as fibronectin, and the like.

The collagen dispersion is formed into a collagen sponge by first pouring the dispersion into appropriate trays having a height which will ultimately affect the thickness of the final membrane matrix. Typically, on order to have a final product having a thickness in the range of about 0.2 mm +/−0.05 mm, the height of the tray, which in turn determines the height of the collagen sponge, is about 10 mm +/−3 mm.

The trays containing the dispersion are then placed in a freezer maintained at a temperature of from about −10° C. to about −40° C. for a length of time sufficient to freeze the water that is present in the dispersion, generally for about 1 to about 24 hours.

The thusly frozen dispersion is then subjected to lyophilization conditions so as to remove the frozen water. This freeze drying is carried out by placing the trays containing the frozen dispersion in a vacuum dryer maintained at a vacuum of about 50 to about 300 microns of Hg at a temperature of from about −10° C. to about −50° C. for about 48 to about 96 hours and then raising the temperature to about 10° C. to about 30° C., preferably 25° C., for about another 10 to 30 hours, preferably about 12 to 24 hours. In this manner, the frozen water sublimes from the solid state immediately to the vapor state leaving behind the desired sponge matrix structure.

The thusly formed sponge matrix structure is then subjected to controlled humidification conditions such that it absorbs a predetermined amount of water. Generally, the amount of water uptake that is desirable as a result of subjecting the sponge matrix to the humidification conditions is in the range of from about 10% to about 30% by weight, based on the weight of the dry sponge, and preferably is in the range of from about 15% to about 25% by weight.

Such water uptake by the sponge matrix can be obtained by exposing the sponge matrix in a controlled humidity chamber for an effective amount of time to achieve the desired water uptake. Generally, the sponge matrix material is placed in a humidity chamber maintained at a relative humidity of from about 78% to about 94% at a temperature of from about 20° to about 30° C., preferably at a temperature of 25° C., for about 10 to about 65 minutes. The specific combination of relative humidity and time of exposure is not critical to the invention provided that the desired amount of water uptake is obtained. Too much water uptake is undesirable as it produces a final product which has the physical characteristics of a conventional collagen film. Conversely, too little water uptake is also undesirable in that it may provide reswelling problems after the forthcoming cross-linking step.

To aid in obtaining more uniform water uptake throughout the sponge matrix material, it is desirable to suspend the sponges in the humidity chamber by any suitable means. Any conventional humidity chamber is applicable for the purpose of this humidification step.

This humidification step is a necessary prerequisite to the immediately following compression step. The humidification of the sponge matrix material provides a cohesiveness which facilitates the compressed sponge to remain in the compressed thickness.

The humidified collagen sponge matrix material is then subjected to a compression step. The collagen sponge matrix material is compressed utilizing any convenient and conventional method such as by placing the sponge in a press, between two rollers, and the like. The amount of compression of the sponge material should desirably be calibrated to a predetermined amount so as to obtain a particular bulk density in the compressed sponge. Manifestly, the more compression of the sponge, the more dense the collagen matrix material will become. However, depending upon the height of the original sponge and the degree of compression, the compressed sponge will desirably have a bulk density in the range of from about 0.5 to about 1.5 g/cc, and preferably in the range of from about 0.8 to about 1.2 g/cc.

Typically, with an initial sponge height of from about 7 mm to about 13 mm, it is compressed to a height of from about 0.15 mm to about 0.25 mm, preferably to a height of from about 0.17 mm to about 0.23 mm.

Essentially no water is removed during the above compression step. As noted earlier, the water acts as a sort of binder to help retain the sponge in its compressed form.

The compressed sponge matrix material is then subjected to a chemical cross-linking step. The cross-linking may be in the liquid or in the vapor phase, with the liquid cross-linking being preferred inasmuch as it provides for more intimate contact of the cross-linking agent with the compressed sponge matrix material.

When collagen is dispersed in an acid solution, many of the acid labile crosslinks become broken. When the collagen is then reconstituted into a new form, additional crosslinks must be formed in order to restore the unique properties in the fibers. This can be done with chromium sulfate, formaldehyde, glutaraldehyde, carbodiimide, adipyl dichloride, and the like, and is commonly known as tanning. The rate at which the collagen membranes of the present invention is resorbed in vivo in a mammal, the structural integrity of the membrane and its mechanical strength is dependent, among other things, on the degree of tanning. Factors controlling the extent of crosslinking or tanning are the type and concentration of the tanning agent when utilized in the liquid phase or the vapor pressure of the tanning agent when utilized in the vapor phase, and the pH and the temperature of incubation. Desirably, the collagen membranes of the present invention are crosslinked to such an extent that they are completely resorbed within about 4 to about 8 weeks.

The degree of tanning can be measured by the hydrothermal shrink temperature (Ts) of the membrane, i.e., the temperature at which the membrane in an aqueous environment begins to shrink, or by its susceptibility to enzyme digestion, i.e., the more crosslinked the collagen, the longer it will take to digest. The enzyme normally used for enzyme digestion measurement is collagenase.

Generally, the degree of tanning is such that the shrink temperature of the collagen membrane material is in the range of from about 55° to about 75° C., preferably from about 60° to about 65° C.

In one embodiment of the present invention, the compressed collagen sponge is cross-linked by immersing the sponge in a 0.5% formaldehyde solution, 1.0% sodium bicarbonate solution at a pH of 8.0+/−0.2 for 60+/−5 minutes in a cross-linking chamber.

The crosslinked compressed sponge matrix material is then thoroughly washed with deionized, ultrafiltered water to remove any excess tanning agent when the tanning agent is utilized in the liquid phase. If used in the vapor phase, the sponge material is alternatively subjected to evacuation to remove residual tanning agent.

At this point in the process, the rinsed, compressed sponge matrix material generally has an overall thickness in the range of from about 0.30 mm to about 0.45 mm.

In accordance with the method for preparing the dense collage matrix material of the present invention, the compressed sponge matrix material, after being washed to remove residual tanning agent, is then once again subjected to the steps of freezing, freeze drying, humidification and subsequent recompression. It is this further series of processing steps, in combination with the preceding series of steps, which is most important in providing the desired opaqueness of the dry material and the translucency of the wet membrane material of the present invention as well as its leather-like morphology which is essential in providing for its good handleability.

Accordingly, the washed collagen matrix material is then refrozen in a manner similar to and under the same conditions as in the first freezing step. Specifically, the washed, collagen material is placed in a freezer maintained at the same temperature as that of the first freezing step, namely, from aobut $-10°$ to about $-40°$ C. The time, however, the amount of residence time in the freezer is less than that for the first freezing step. Typically, the amount of freezing time is about one-half that of the first freezing step, generally from about ½ to 12 hours.

The thusly frozen compressed sponge is then once again subjected to a lyophilization step. The conditions for carrying out this further freeze-drying step are essentially the same as that utilized in the first drying step but as in the freezing step, the residence time required for this second freeze-drying step is much shorter than the first. Particularly, the vacuum dryer is maintained at a vacuum of about 50 to about 200 microns of Hg at a temperature of from about $-10°$ C. to about $-50°$ C. The period for this second freeze-drying step is in the range of from about 24 to about 48 hours. Just as in the first freeze-drying step, the temperature is then raised to about 10° C. to about 30° C., preferably 25° C. This time, however, the matrix material is subjected to this higher temperature for an additional period of about 5 to 15 hours, preferably about 7 to 12 hours. In this manner, the frozen water sublimes from the solid state immediately to the vapor state leaving behind the dried collagen matrix structure.

This secondary refreezing and refreeze-drying of the compressed collagen matrix material helps preserve the sponge characteristics which, in turn, is responsible for providing the dense collagen matrix material product with the desirable properties of better handleability and feel, surface roughness, and translucence.

The thusly dried collagen matrix is then resubjected to humidification condition similar to the first humidification step. In this second humidification step, the amount of time for such humidification is shorter. Accordingly, the dried matrix material is then once again placed in a humidity chamber maintained at a relative humidity of from about 78% to about 94% at a temperature of from about 20° to about 30° C., preferably about 25° C. This time, the residence period in the humidity chamber is for about 5 to about 30 minutes. The amount of water taken up by the dried matrix material is generally in the range of from about 10% to about 30%, based on the weight of the dried material, and preferably is in the range of from about 15% to about 25%.

This second humidification step aids to relieve stresses in the matrix material and to provide a more uniform, flat appearance to the membrane. Moreover, the water also acts as a binding agent and softener to allow for the subsequent recompression step.

As the final step in the method, the rehumidified collagen matrix material is then recompressed to the desired, final thickness which is desirable for the particular end use contemplated. As in the first compression step, rollers, plates, and the like, may be used to accomplish this further compression step.

Generally, the matrix material is compressed from a starting thickness, subsequent to the rehumidification step, of from about 0.30 to about 0.45 mm, to a final thickness of from about 0.15 to about 0.25 mm, preferably from about 0.17 to about 0.23 mm. The final bulk density of the dense collagen matrix material is typically in the range of from about 0.5 to about 1.5 g/cc, and preferably is from about 0.8 to about 1.2 g/cc.

By virtue of having made the dense collagen matrix materials in accordance with the above procedure, the pore size of the matrix material is such that it is semi-permeable to the extent that it will selectively diffuse certain desired constituents while advantageously prevent others from getting through. More specifically, in order to accomplish this desired selectivity, the pore size of the semi-permeable dense collagen matrix membrane is in the range of from about 0.003 $\mu$m to about 0.10 $\mu$m, and preferably is in the range of from about 0.005 $\mu$m to about 0.01 $\mu$m. This pore size enables nutrients and macromolecules to diffuse through the membrane while at the same time prevent the introduction of undesirable elements such as epithelium and gingival connective tissue in the case of periodontal therapy.

In use, the dense collagen matrix membranes of the present invention, unlike conventional collagen films, do not have a slimy-type feel associated with them upon being wetted. Instead, they have a surface roughness morphology which is not unlike that of leather. Moreover, unlike conventional collagen films which are transparent both when dry and when wet, the collagen matrix membranes of the present invention are opaque when dry. When wetted, the collagen matrix membranes of the present invention are translucent. Still further, the collagen matrix membranes have excellent structural integrity, both when wet and dry. This combination of properties is particularly advantageous to the user inasmuch as it allows for easy handling throughout any surgical procedure.

Once utilized, it advantageously does not appreciably swell, retaining its predetermined bulk density, thereby desirably not affecting the integrity of the surgical site, regardless of its specific end use, i.e., whether it is being used as a periodontal barrier, a medicament carrier, a hemostat, or the like. So too, because of its predetermined permeability, which selectively permits the diffusion of desirable constituents to the surgical site, rapid healing is provided. Lastly, by means of the present invention, a highly controllable rate of resorption is also obtainable for controlled wound healing.

EXAMPLES

Example I

Preparation of Type I collagen dispersion

After the fat and fascia were carefully cleaned from bovine flexor tendons and washed with sodium dodecyl sulfate detergent solution, they were frozen and sliced into approximately 0.5 mm slices with a meat slicer. The tendon slices were then digested in ficin for 1 hour at 37° C. (collagen:enzyme being about 150:1 w/w). The ficin was subsequently inactivated by adding $NH_4NO_3$ and $NaClO_2$. The slices were thoroughly washed with deionized, ultrafiltered water to eliminate excess enzymes and non-collagenous impurities.

The collagen was then dispersed in a 0.5% lactic acid solution for about 30 min. The dispersed collagen was then blended in a Waring blender to further dissociate the fibers into a more uniform dispersion. The collagen dispersion was then filtered through a 100 stainless steel mesh screen to define the particle size of the swollen collagen. The final collagen concentration of the dispersion is about 0.7% by weight.

Example II

Preparation of Collagen Sponge 3.5 liters of collagen dispersion from Example I was poured into a freeze drying tray (20"×21") for the production of a 10 mm thick sponge.

The dispersion was allowed to freeze on the shelf for two hours at −35° C. before pulling the vacuum. The frozen dispersion was then freeze dried under approximately 100 u vacuum for 72 hours. The shelf temperature was subsequently raised to 25° C. for approximately 24 hours to complete the freeze drying process.

The freeze dried sponge was used in Example III for preparation of the dense membrane matrix in accordance with the present invention.

Example III

Preparation of Dense Collagen Membrane Matrix

The 20"×21"×0.40" sponges from Example II were placed in a controlled humidity chamber with a relative humidity of 80% at 25° C. for 60 minutes. The net moisture uptake by the sponges was 20% of the dry sponge weight.

The moist collagen sponges were then compressed in a roller press twice between two PTFE (Teflon) sheets with a calibrated aperture of about 0.20 mm. The compressed collagen sponge was then cross-linked in a solution of 0.5% formaldehyde, 1% bicarbonate at pH of 8.0 for 60 minutes in a cross-linking chamber.

The cross-linked sponges were rinsed thoroughly with ultra-filtered water (6 liters/sponge). The rinsed solutions were changed at 30, 30, 60, and 60 minutes and at 16 hours.

The wet sponges were freeze dried overnight under similar conditions as in Example II except that the time for freeze drying was reduced to half of the sponge production method. The freeze dried sponges were then again humidified with a relative humidity of 80% at 25° C. for 15 minutes.

The moist freeze dried dense membrane matrices were then subjected to a second compression with an aperture of approximately 0.20 mm. The final compressed dense membrane matrices were cut to a size of 1.5"×0.75" (3.8×1.9 cm) and packaged for sterilization.

Example IV

Characteristics of Dense Membrane Matrix

The properties of the dense membrane matrix prepared in Example III were characterized. The procedures for the characterization and a summary of the properties are set forth below:

a) Apparent Density

Dense membrane matrices were cut to the exact size of 1.5"×0.75" (3.8×1.9 cm).

The thickness of the membranes were measured with a thickness gauge.

The volume of the membranes was calculated from the length, width and thickness data.

The weight of the membranes was determined from an analytical balance.

The apparent density of the membrane was defined as: $\rho = m/v$, where $\rho$=apparent density; m=weight of dense membrane matrix and v=calculated volume from the dimension data.

b) Solution Uptake

The weight of a dense membrane matrix was measured on an analytical balance. The weighed membrane was then immersed in a phosphate buffered saline solution (PBS), at a pH of 7.0 and 25° C. for 30 minutes.

The membrane was removed from the PBS solution and the wet membrane was weighed again on an analytical balance. The net solution uptake of the membrane was calculated as the difference between the wet and dry weights of the membrane.

c) Suture Pull-Out Strength

A dumbbell shaped collagen dense membrane matrix was cut using a dumbbell die under pressure. The cut membrane was then immersed in a phosphate buffered saline solution at a pH of 7.0 at 25° C. for 10 minutes.

One end of the membrane was pierced 3 mm from the end with a general closure needle and the suture thread was clamped in the upper grip of a tensile tester. The other end of the membrane was inserted in the lower grip 3 mm from the end.

The stress was applied at a rate of 1 cm/sec until the breaking point was reached and the total stress was recorded.

d) Bending Strength

Dense membrane matrices were cut into 1.5"×0.75" rectangles. A portion of a membrane was fixed at the edge of a surface leaving 1.2 cm length of the membrane extended out from the edge without support. Small weights were then slowly attached at the edge of the extended portion of the membrane.

A protractor was attached at the edge of the surface to measure the extent of bending of the membrane. The total weight needed to bend a 45 degree angle was recorded.

e) Shrinkage Temperature

Dense membrane matrices were cut to sizes of 1.5"×0.4" rectangles. Approximately 1 liter of a phosphate buffered saline solution (PBS) at a pH of 7.0 was poured into a beaker and a stir bar was inserted into the solution. The solution was heated to approximately 46° C. on a stirrer-hot plate.

On the conventional shrinkage temperature apparatus, a membrane was clamped in the lower clamp and a closure needle was inserted in the upper end of the membrane leaving a distance of approximately 3 cm between the clamp and the closure needle. Once the temperature reached approximately 46° C., the membrane was immersed in the PBS solution and the temperature of the solution and the length of the membrane were recorded at approximately 0.5°–1° C. intervals until the membrane was fully denatured and a constant reading was reached.

The shrinkage temperature was defined as that temperature in which a 50% change in the sample length was observed on a shrinkage curve (length vs. temperature plot).

f) Permeability

Dense membrane matrices were cut to sizes of 1.5"×1.5" squares and immersed in a beaker containing 0.05M Tris buffer at a pH of 7.4 at 25° C. for approximately 15 minutes. The membrane was then cut to fit in the gap between two chambers. Chamber 1 was filled with a 0.25%–1% testing solution of glucose, myoglobin, bovine serum albumin (BSA), $\beta$-galactosidase or dextran and chamber 2 was filled with 0.5M Tris buffer at a pH of 7.4.

Aliquot solutions were collected from chamber 2 at 2, 6, 24, 48 and 72 hours and assayed for the concentration of glucose, myoglobin, BSA, $\beta$-galactosidase and dextran with colorimetric method developed for these molecules using a spectrophotometer.

Absorbance was read on a spectrophotometer at 625 nm for glucose and dextran and at 595 nm for glucose, BSA and $\beta$-galactosidase.

g) Light Transmittance

The dense membrane matrices were cut to sizes of 1.5"×0.4" (3.8×1.0 cm) and placed in the inner walls of cuvettes of a spectrophotometer. The percentage transmittance was read at a wavelength of 550 nm while fully hydrated.

h) Rolling Resistance

Dense membrane matrices were cut to sizes of 1.25"×7" (3.2×17.8 cm) and immersed in distilled water for 30 minutes. The wet membrane was placed at one end of a 1.25" wide by 23" long plastic track. A metal cylinder (diameter of 2.5 cm, length of 2.0 cm, and weight of 75 grams) was then put in the middle of the wet membrane with the longitudinal direction of the cylinder (Z axis) perpendicular to the longitudinal axis of the membrane. The other end of the track was slowly elevated until the cylinder just began to roll. The maximum height overcame by the rolling resistance was then reached. The rolling resistance was calculated by using the equation $b=(Pr)/W$, where B=rolling resistance, P=horizontal force, r=radius of cylinder, and W=weight of cylinder.

The results of the characterization tests are as follows:

| Apparent Density | 0.96 g/cc |
|---|---|
| Solution Uptake | 2.2 g/g |
| Suture Pull-out | 64 g |
| 45° bending strength | 15 g |
| Shrinkage Temp. | 65° C. |
| Pore size | 0.007 um |
| Light Transmittance | 1% |
| Rolling resistance | 0.24 mm |

Example V

Resorption Evaluation of Dense Membrane Matrix

Dense membrane matrices were cut to sizes of 0.4"×0.4" (1×1 cm) squares and implanted subcutaneously in the upper back areas of adult male Sprague-Dawley albino rats. At 2, 4, 5, 6 and 7 weeks post-operation, animals were sacrificed and the implant sites examined for material size, material consistency and tissue reaction.

At the end of 2 weeks post-implantation, the membrane remained the same size and firm. At 4 weeks, 75–80% of the membrane remained firm. The membrane resorbed faster during 4–7 weeks with approximately 25% of the membrane remaining at 6 weeks and being totally resorbed at the end of 7 weeks. There was only a very mild inflammatory response and normal tissue healing was observed throughout the surgery and repair procedure. This rate of resorption is ideal for guided tissue regeneration applications in periodontal surgery, since no foreign material is left after the regeneration of the periodontal tissue.

Example VI

Preparation of Collagen Film

Comparison Example 5.4 liters of dispersion from Example I was measured into a 20 liter container. 6.0 ml of 85% lactic acid, 400 ml of methanol, 0.5 ml of glycerol and 6.2 liters of ultrafiltered water were added to the dispersion. Once the dispersion was mixed, it was poured into a 12.5"×71" aluminum frame, sitting on a plastic sheet, under a laminar flow hood and allowed to dry for approximately 7 days to from a collagen film, typically of 0.1 mm thickness.

After the film was dried, the film was neutralized with 3.0 liters of 0.3% ammonium hydroxide for 30 minutes. The neutralized film was rinsed four times and soaked overnight in ultra-filtered water. The rinsed film was dried overnight under a laminar flow hood.

Example VII

Characteristics of Conventional Collagen Film

Comparison Example

The film prepared in Example VI, which is not in accordance with the present invention, was characterized in the same manner as the dense collagen matrix material of the present invention. The results of those test are as follows:

| Apparent Density | 2.1 g/cc |
|---|---|
| Solution Uptake | 1.1 g/g |
| Suture Pull-out | 230 g |
| 45° Bending Strength | 2.9 g |
| Pore size | less than .003 μm |
| Light Transmittance | 82.4% |
| Rolling Resistance | 0.14 mm |

Example VIII

Clinical Use of Collagen Dense Membrane Matrix

Male and female patients with advanced periodontitis were included in the study. Patients with at least one pair of similar contralateral periodontal lesions with probing depths of $\geq 5$ mm and radiographic evidence of $\geq 40\%$ bone loss were included. Each patient underwent contralateral surgical flap procedures, which included thorough debridement and bone defect depth measurements. At the test site, a collagen dense membrane matrix was carefully adapted to the defects and covered an existing infrabony defects entirely and extend approximately 1 mm over the alveolar bone crest. The membranes were trimmed at the coronal margin of the flap and the flaps were replaced and sutured. The controls consisted of the same procedure without the placement of the membrane. Standardized measurements of gain in clinical attachment and fill of intrabony defects were obtained at the time of surgery and one year later at the time of surgical re-entry. Ninety two pairs of measurements were obtained for statistical analysis. The difference in gain of clinical attachment between individual test and control sites was 1.25+/−0.22 mm and the amount of bone fill in intrabony defects was 1.28+/−0.28 mm. The results of this study demonstrated that test sites treated with the membrane matrix prepared in accordance with the present invention had significantly better results as compared to the control sites in which no membrane was used.

What is claimed is:

1. A method of making a dense collagen membranous matrix material which when wetted with water is translucent and non-slippery comprising the steps of:
   a) forming an aqueous dispersion containing insoluble Type I collagen;
   b) freezing the aqueous dispersion;
   c) subjecting the frozen dispersion to freeze-drying conditions to remove frozen water and form a collagen sponge matrix;
   d) subjecting the collagen membranous matrix to humidification conditions for a time period of about 10 to about 65 minutes, such that the collagen membranous matrix absorbs about 10% to about 30% water by weight based on the weight of the collagen membranous prior to the humidification step;
   e) compressing the humidified collagen membranous matrix;
   f) cross-linking the compressed collagen matrix in either a liquid or vapor phase by treatment with a cross-linking agent selected from the group consisting of chromium sulfate, formaldehyde, glutaraldehyde, carbodiimide and adipyl dichloride, by immersing the collagen matrix in a solution of the cross-linking agent and then substantially removing the cross-linking agent;
   g) refreezing the cross-linked collagen matrix;
   h) resubjecting the frozen collagen matrix to freeze-drying conditions to remove frozen water;
   i) resubjecting the dried cross-linked collagen matrix to humidification conditions comprising a for a time period of about 5 to about 30 minutes; and then
   j) further compressing the humidified, collagen matrix to form the dense collagen membrane matrix material.

2. The method of claim 1, wherein the Type I collagen is obtained from bovine tendons.

3. The method of claim 1, wherein the dispersion contains medicaments.

4. The method of claim 3, wherein the medicaments include antibiotics, heparin, heparan sulfate proteoglycan glycosaminoglycans epidermal growth factor, and/or glycoproteins.

5. The method of claim 1, wherein freezing step (b) is carried out at a temperature in the range of from about −10° C. to about −40° C. for a period of from about 1 to about 24 hours.

6. The method of claim 1, wherein freeze drying step (c) is carried out under by subjecting the frozen dispersion to a vacuum of from about 50 to about 300 microns Hg, at a temperature of from about −10° C. to about −50° C., for a period of about 48 to about 96 hours and then raising the temperature to about 10° C. to about 30° C. for about 10 to about 30 hours.

7. The method of claim 1, wherein the amount of water absorbed in step (d) is in the range of from about 15% to about 25% water by weight, based on the weight of the collagen membranous matrix prior to the humidification step.

8. The method of claim 1, wherein the humidification conditions of step (d) include a relative humidity of about 78% to about 94%, and a temperature of about 20° to about 30° C.

9. The method of claim 1, wherein the humidified collagen membranous matrix is compressed in step (e) to a bulk density in the range of from about 0.5 to about 1.5 g/cc.

10. The method of claim 9, wherein the collagen membranous matrix is compressed to a bulk density in the range of from about 0.8 to about 1.2 g/cc.

11. The method of claim 1, wherein the humidified collagen membranous matrix is compressed in step (e) to a thickness in the range of from about 0.15 mm to about 0.25 mm.

12. The method of claim 11, wherein the thickness is in the range of from about 0.17 mm to about 0.23 mm.

13. The method of claim 1, wherein the degree of cross-linking is such that the collagen material has a shrink temperature in the range of from about 55° C. to about 75° C.

14. The method of claim 13, wherein the shrink temperature is in the range of from about 60° C. to about 65° C.

15. The method of claim 1, wherein the degree of cross-linking is such that the collagen material is resorbed within about 4 to about 7 weeks.

16. The method of claim 1, wherein freezing step (g) is carried out for about 0.5 to about 12 hours at a temperature in the range of from about −10° C. to about −40° C.

17. The method of claim 1, wherein freeze-drying step (h) is carried out for about 24 to about 48 hours at a temperature in the range of from about −10° C. to about −50° C., at a vacuum of from about 50 to about 300 microns Hg, and then raising the temperature to about 10° C. to about 30° C. for about 5 to about 15 hours.

18. The method of claim 1, wherein the humidification conditions of step (i) include a relative humidity of about 78% to about 94%, a temperature of about 20° to about 30° C.

19. The method of claim 1, wherein the humidification conditions of step (i) are such that the collagen matrix absorbs about 10% to about 30% water by weight, based on the weight of the collagen matrix prior to the humidification step.

20. The method of claim 19, wherein the about of water absorbed is in the range of from about 15% to about 25% water by weight, based on the weight of the collagen matrix prior to the humidification step.

21. The method of claim 1, wherein the humidified collagen matrix is compressed in step (j) to a bulk density in the range of from about 0.5 to about 1.5 g/cc.

22. The method of claim 21, wherein the collagen matrix is compressed to a bulk density in the range of from about 0.8 to about 1.2 g/cc.

23. The method of claim 1, wherein the humidified collagen membranous matrix is compressed in step (j) to a thickness in the range of from about 0.15 mm to about 0.25 mm.

24. The method of claim 23, wherein the thickness is in the range of from about 0.17 mm to about 0.23 mm.

25. The dense collagen membrane matrix material produced by the method of claim 1 having a pore size in the range of from about 0.003 μm to about 0.10 μm.

26. A dense collagen membrane matrix material made by the method of claim 1 characterized by being translucent and non-slippery when wetted with water.

27. A dense collage membranous material made by the method of claim 1 having a density of from about 0.5 to about 1.5 g/cc; a rolling resistance of from about 0.15 to about 0.5 mm; a light transmittance of from about 0 to about 10% when fully hydrated; and a pore size in the range of from about 0.003 μm to about 0.10 μm.

28. A method of treating a patient having periodontitis by surgically exposing the root surface of a tooth, debriding the exposed area and placing a membrane over the debrided root surface so as to prevent epithelium and gingival connective tissue from contacting the root surfaces during healing, the improvement which comprises using a collagen membrane matrix made according to the method of claim 1 having an apparent density of from about 0.5 to about 1.5 g/cc, which when wetted with water is translucent and non-slippery.

* * * * *